United States Patent
Yang et al.

(10) Patent No.: US 10,221,403 B1
(45) Date of Patent: Mar. 5, 2019

(54) METHOD OF PREPARING ZEARALENONE HYDROLASE

(71) Applicant: Life Rainbow Biotech Co., Ltd., Yilan County (TW)

(72) Inventors: Ching-Kuo Yang, Yilan County (TW); Yu-Hsiang Yu, Yilan County (TW); Ya-Chieh Huang, Yilan County (TW); Rou-Wan Liao, Yilan County (TW)

(73) Assignee: LIFE RAINBOW BIOTECH CO., LTD., Yilan County (TW)

( * ) Notice: Subject to any disclaimer, the term of this patent is extended or adjusted under 35 U.S.C. 154(b) by 0 days.

(21) Appl. No.: 15/962,085

(22) Filed: Apr. 25, 2018

(51) Int. Cl.
| | |
|---|---|
| *C12N 9/18* | (2006.01) |
| *C12N 15/00* | (2006.01) |
| *C12N 1/20* | (2006.01) |
| *C12P 21/06* | (2006.01) |
| *C12P 21/04* | (2006.01) |
| *C07H 21/04* | (2006.01) |
| *C12N 1/14* | (2006.01) |
| *C12N 15/81* | (2006.01) |
| *C12N 1/16* | (2006.01) |

(52) U.S. Cl.
CPC ............... *C12N 9/18* (2013.01); *C12N 1/16* (2013.01); *C12N 15/81* (2013.01); *C12N 15/815* (2013.01); *C12Y 301/01* (2013.01)

(58) Field of Classification Search
None
See application file for complete search history.

(56) References Cited

U.S. PATENT DOCUMENTS

2016/0039911 A1* 2/2016 Lesnicki ............... C07K 16/00
435/69.6

FOREIGN PATENT DOCUMENTS

CN 102586340 * 7/2012
WO WO 2016/183163 * 11/2016

OTHER PUBLICATIONS

Studer. Residue mutations and their impact on protein structure and function: detecting beneficial and pathogenic changes. Residue mutations and their impact on protein structure and function: detecting beneficial and pathogenic changes. Biochem. J. (2013) 449, 581-594.*
Vekiru. Isolation and characterization of enzymatic zearalenone hydrolysis reaction products. World Mycotoxin Journal, 2016; 9 (3): 353-363.*
Wu. Machine translation of CN 102586340. retrieved from Google on Jun. 8, 2016.*
Shahidan The effect of carbon sources on the expression level of thermostable L2 lipase in Pichia pastoris. African Journal of Biotechnology vol. 10(62), pp. 13528-13535, Oct. 12, 2011.*
Naoko Takahashi-Ando et al., "Metabolism of Zearalenone by Genetically Modified Organisms Expressing the Detoxification Gene from Clonostachys rosea", Applied and Environmental Microbiology, Jun. 2004, p. 3239-3245.

(Continued)

*Primary Examiner* — Yong D Pak
(74) *Attorney, Agent, or Firm* — WPAT, PC

(57) ABSTRACT

The present invention provides a method of preparing zearalenone hydrolase, including the step of culturing a yeast cell carrying a gene encoding a zearalenone hydrolase in a medium to express a protein of the zearalenone hydrolase, wherein the medium contains 20 to 25% molasses by weight. This method provides a new strategy to efficiently prepare zearalenone hydrolase at low expenses.

7 Claims, 2 Drawing Sheets
Specification includes a Sequence Listing.

(56) References Cited

OTHER PUBLICATIONS

Naoko Takahashi-Ando et al., "A novel lactonohydrolase responsible for the detoxification of zearalenone : enzyme purification and gene cloning", Biochem. J. (2002) 365, 1-6 (Printed in Great Britain).

* cited by examiner

METHOD OF PREPARING ZEARALENONE HYDROLASE

BACKGROUND OF THE INVENTION

1. Field of the Invention

The present invention relates to a method of producing recombinant proteins. Particularly, the present invention relates to a method of producing zearalenone hydrolase.

2. The Prior Art

Zearalenone (ZEA), produced in grains infected by *Fusarium* species such as *F. roseum*, is a non-steroidal mycotoxin possessing estrogen activity. The contaminated grains include corn, rice, barley and wheat. Monogastric animals are most highly susceptible to ZEA, followed by ruminants, while poultry is least affected. Among the monogastric animals, pigs are the most seriously harmed. Previous studies on swine breeding have shown that ZEA may cause stillbirth, neonatal mortality, mummified piglets, abortion, and irregular false estrus. The symptoms of the affected sows include vaginal prolapse, enlarged uterus and uterine horns, and ovarian atrophy, and even rectal prolapse in severe cases. This toxin has no significant pathological effect on the appearance of male pigs, but there are studies confirming that male piglets are affected and exhibit testicular atrophy, penile foreskin inflammation, mammary gland swelling, and decreased libido. These serious effects of ZEA on pig reproduction may be explained by the species specific metabolism of this toxin. ZEA is metabolized in pig liver mainly to α-zearalenol (α-Zol), which has higher estrogen activity than other ZEA derivatives such as α-zearalanol (α-Zal) and β-zearalenol (β-Zol) found in poultry, cattle, and sheep.

To reduce ZEA contamination to grains, several approaches have been employed, for example, dilution of the contaminated feed, use of fungicides that inhibit mold growth, toxin absorption by aluminum silicate, toxin degradation by heating and extrusion, microbial transformation, and the production of gene-modified crops that degrade ZEA. The cultivation of gene-modified crops, which leads to thorough prevention of plant infection in the fields, might be the most promising treatment, but the impact of these crops is hard to estimate.

In 2002, Takahashi-Ando et al. found that the soil fungus *Clonostachys rosea* IFO 7063 effectively reduced the ZEA levels, and a gene encoding a ZEA-hydrolyzing enzyme was isolated and named zearalenone hydrolase (ZHD101). It is hypothesized that this enzyme acts by breaking down the lactone ring of ZEA, causing the exposure of carboxyl and hydroxyl groups, and promoting secondary product formation through carboxylation. The secondary products have been shown to have no estrogenic effect on human breast cancer cells lines (MCF-7).

Takahashi-Ando et al. (2004) has established a prokaryotic protein expression system for the ZHD101 gene by using *Escherichia coli*. However, there are biosafety concerns of using bacteria as hosts to produce proteins for detoxifying foods or animal feeds. Furthermore, other issues such as fermentation time limit and medium costs need to be considered when the process of microbial production of zearalenone hydrolase is scaled up for industrial use. Therefore, it is of necessity to explore alternative methods of preparing the zearalenone hydrolase.

SUMMARY OF THE INVENTION

As a result, the present invention provides a method of preparing zearalenone hydrolase, including the step of culturing a yeast cell carrying a gene encoding a zearalenone hydrolase in a medium to express a protein of the zearalenone hydrolase, wherein the medium contains 20 to 25% molasses by weight.

In one embodiment, the yeast cell is *Pichia pastoris*; the gene encoding the zearalenone hydrolase is inserted into an inducible expression vector; the expression of the zearalenone hydrolase is induced by adding methanol into the medium, and the methanol in the medium is at a concentration of 0.25 to 0.75%.

In another embodiment, the yeast cell is cultured at 28° C. to 30° C. for 24 to 72 hours with agitation at 100 to 150 rpm.

In still another embodiment, the medium further includes urea, ammonium dihydrogen phosphate, thiamine, or any combinations thereof.

In yet another embodiment, the method further includes the step of isolating the zearalenone hydrolase from the yeast cell or the medium after the culturing. For example, the zearalenone hydrolase is isolated by lysing the yeast cell and collecting a supernatant of a cell lysate obtained therefrom.

Compared to the conventional methods of preparing recombinant zearalenone hydrolase, the method of the present invention utilizes the molasses-containing medium to induce the high production of zearalenone hydrolase by yeast in three days. Therefore, the present invention provides a new strategy to prepare zearalenone hydrolase efficiently at low expenses.

The present invention is further described in the following examples, in reference to the accompanying drawings. It should be understood that the examples given below do not limit the scope of the invention, and that modifications can be made without departing from the scope of the appended claims.

BRIEF DESCRIPTION OF THE DRAWINGS

The present invention will be apparent to those skilled in the art from the following detailed description of the preferred embodiments, with reference to the accompanying drawings, in which.

DETAILED DESCRIPTION OF THE PREFERRED EMBODIMENT

Definition

Figure 1:
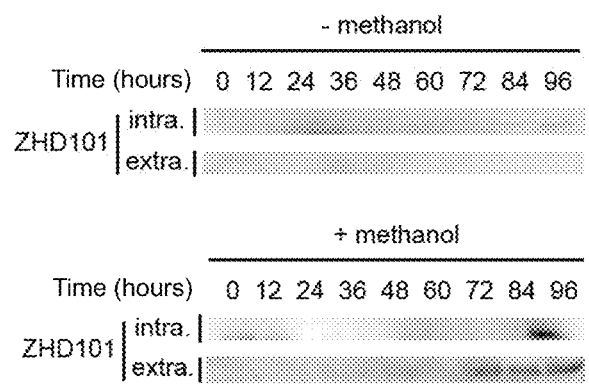
FIG. 1 shows western blot images indicating the intracellular and extracellular zearalenone hydrolase (ZHD101) expression by a transformed *P. pastoris* cultured for the indicated time in a BMMY medium with or without methanol added.

The data provided in the present invention represent approximated, experimental values that may vary within a range of ±20%, preferably ±10%, and most preferably ±5%.

The expression "yeast cells" used herein refers to the cells of any yeast strains that are engineered by recombinant DNA technology for the expression of exogenous proteins.

The present invention provides a method of preparing zearalenone hydrolase, including the step of culturing yeast cells carrying a gene encoding zearalenone hydrolase in a medium to promote protein expression of the zearalenone hydrolase. Details of the present invention are provided below.

Methods and Materials

Molasses

Molasses was purchased from local suppliers. In one embodiment, the molasses contains 30% sucrose, 15% glucose, and 15% fructose.

Preparation of Zearalenone Hydrolase Expression Vector

To prepare a zearalenone hydrolase expression vector for transformation of yeast cells, a gene encoding zearalenone hydrolase (ZHD101) and having the nucleotide sequence of SEQ ID NO:1 is cloned into an expression vector containing a methanol inducible promoter, for example, the pPICZα vector (Thermo Fisher Scientific). To facilitate protein purification, the gene may further include a short DNA sequence encoding numbers of histidine, which is termed a His tag.

Sodium Dodecyl Sulfate Polyacrylamide Gel Electrophoresis (SDS-PAGE)

SDS-PAGE was performed as follows. In brief, gels for electrophoresis were prepared by casting a 15% separating gel (2.5 ml of 1 M Tris (pH 8.8), 2.3 ml deionized water, 5 ml of 30% acrylamide mix, 0.1 ml of 10% SDS, 0.1 ml of 10% ammonium persulfate (APS), and 0.05 ml TEMED) and a 4% stacking gel (0.63 ml of 1 M Tris (pH 6.8), 3.4 ml deionized water, 0.83 ml of 30% acrylamide mix, 0.05 ml of 10% SDS, 0.05 ml of 10% APS, and 0.005 ml TEMED). At the same time, protein samples from yeast cells (referred to as intracellular protein samples) or those from yeast culture media (referred to as extracellular protein samples) were mixed at equal volume with SDS-loading buffer (100 mM Tris-HCl (pH 6.8), 200 mM dithiothreitol (DTT), 4% SDS, 0.2% bromophenol blue, 20% glycerol, and 10% (v/v) 2-mercaptoethanol) and heated to 100° C. for 10 minutes. Electrophoresis was performed at 70V for stacking and at 110V for separating.

Western Blotting

Western blotting was performed as follows to verify the intracellular and extracellular zearalenone hydrolase production. The SDS-PAGE gel containing the separated intracellular or extracellular protein samples and a polyvinylidene difluoride (PVDF) membrane (Immobilon™-P Transfer Membrane, Millipore) were sandwiched between sponge and paper and clamped tightly to form a sandwich, which was then submerged in transferring buffer (200 mM Glycine, 20% Methanol, 25 mM Tris-HCL, pH 8.3). The protein samples were transferred to the PVDF membrane at 1.2 mA/cm$^2$ for 45 minutes. The membrane was then incubated in phosphate buffered saline with Tween-20 (referred to as PBST; 137 mM sodium chloride, 2.7 mM potassium chloride, 4.3 mM sodium hydrogen phosphate, 1.4 mM potassium dihydrogen phosphate, and 0.5% Tween-20, pH 7.4) supplemented with 5% skimmed milk to block the nonspecific binding for at least one hour. After washed three times with PBST, the membrane was incubated overnight with mouse anti-His tag antibody (2633; Cell Signaling Technology) at a dilution factor of 1:1000 in PBST at 4° C. After washed three times with PBST, the membrane was incubated with horseradish peroxidase (HRP)-conjugated goat anti-mouse immunoglobulin G (IgG) secondary antibody (GTX213111-01; GeneTex) at a dilution factor of 1:10000 in PBST at room temperature with shaking for one hour, and washed three times with PBST. For detection, an enhanced chemiluminescence (ECL) reagent (PerkinElmer) was added to the membrane to produce luminescence signals, which was visualized on an X-ray film.

Analysis of Enzymatic Activity

A 250 mL culture of the transformed yeast cells expressing zearalenone hydrolase was first incubated with 0.5% methanol, 1.5 µg/ml zearalenone (Z2125, Sigma) and 1.5 µg/ml α-zearalenol (Z0166, Sigma) at 30° C. for 96 hours for hydrolytic reaction, and 150 µl of the supernatant of the culture medium was mixed at equal volume with 100% methanol. The resultant mixture with a volume of 25 µl was subjected to high-performance liquid chromatography (HPLC)-fluorescence analysis of the hydrolyzed products (excitation wavelength at 271 nm and emission wavelength at 452 nm) after filtration with 0.22 µm Nylon membrane (Chromtech). The mobile phase for HPLC was a mixture of acetonitrile, methanol, and water (10:55:35 by volume) that contained 15 mM ammonium acetate. The column for analysis was reversed-phase C18 column (LiChroCART 250-4, RP-C18; Merck, Germany).

Example 1

Small-Scale Production of Zearalenone Hydrolase in Yeast

A *Pichia pastoris* yeast strain GS115 (ATCC 20864), transformed with a zearalenone hydrolase (ZHD101) expression vector, was inoculated into about 3 to 5 mL of fresh yeast extract-peptone-dextrose (YPD) medium and incubated at 28° C. to 30° C. with agitation at 150 rpm for 24 hours, and 300 µl of this yeast culture was then seeded into 250 ml buffered minimal glycerol yeast (BMGY) medium (1% yeast extract, 2% peptone, 100 mM potassium phosphate buffer (pH 6.0), 1.34% yeast nitrogen base, 4×10$^{-5}$ M biotin, 1% glycerol) to obtain a first culture which was then incubated at 28° C. to 30° C. with agitation at 100 to 150 rpm overnight. After reaching a light absorbance at 600 nm (OD600) of about 2, the first culture was centrifuged at 5000×g for 5 minutes at 4° C., and the resultant cell pellet was collected and resuspended in a molasses-containing medium (TABLE 1) to obtain a second culture. For comparison, another culture was set up where the cell pellet prepared as mentioned above was resuspended in the buffered minimal methanol yeast (BMMY) medium (TABLE 2). After diluted to an OD600 value of about 1, the second culture was incubated at 28° C. to 30° C. with agitation at 100 to 150 rpm for 72 to 96 hours and optionally supplemented with methanol every 24 hours to maintain a final methanol concentration of 0.25 to 0.75% (v/v), preferably 0.5% (v/v).

TABLE 1

Composition of molasses-containing medium

| | |
|---|---|
| Molasses | 20-25% |
| Urea | 1.0-2.5% |
| Ammonium dihydrogen phosphate | 0.5-1.0% |
| Thiamine | 0.25-0.75% |
| Methanol | 0.5% |

TABLE 2

Composition of BMMY medium

| | |
|---|---|
| Yeast extract | 1.0% |
| Peptone | 2.0% |
| Potassium phosphate buffer, pH 6.0 | 100 mM |
| Yeast nitrogen base (YNB) | 1.34% |
| Biotin | $4 \times 10^{-5}$ M |
| Methanol | 0.5% |

To examine the intracellular and extracellular ZHD101 protein production, 5 ml of the second culture was collected every 24 hours and centrifuged at 13,000×g for one minute to separate the yeast cells from the yeast culture medium. For extraction of the intracellular proteins, the yeast cells were lyzed in 100 μl breaking buffer (50 mM sodium phosphate (pH 7.4), 1 mM EDTA, 1 mM phenylmethylsulfonyl fluoride (PMSF), 5% glycerol) by eight cycles of sonication (30 seconds) and cooling on ice (30 seconds), followed by centrifugation of the cell lysate at 13,000×g for 10 minutes to collect a supernatant, that is, the intracellular protein sample. For preparation of the extracellular protein samples, the yeast culture medium was concentrated using Amicon Ultra 15 mL Centrifugal Filters (EMD Millipore). The intracellular and extracellular protein samples were quantified by the Bradford Protein Assay (Bio-Rad) and subjected to SDS-PAGE and western blotting for analysis of the protein expression of ZHD101.

FIG. 1 shows western blot images indicating the intracellular and extracellular ZHD101 expression by the transformed P. pastoris cultured in the BMMY medium with or without methanol. According to FIG. 1, the yeast cultured in the BMMY medium with no methanol added produced little intracellular ZHD101 only after 96 hours of incubation and no detectable extracellular ZHD101. In contrast, the addition of methanol induced both the intracellular and extracellular ZHD101 expression to a much higher extent. The intracellular ZHD101 was detected after 96 hours of incubation with methanol induction, while the extracellular ZHD101 was detected after incubation for 72 hours. This result indicates that only the methanol-supplemented BMMY medium is suitable for the efficient production of ZHD101 by the transformed P. pastoris.

Figure 2:
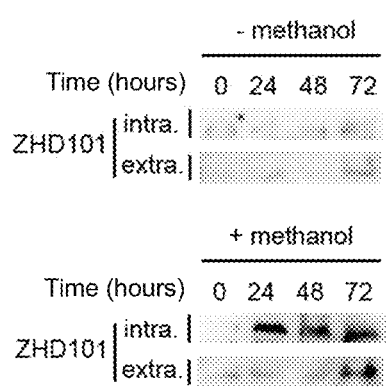
FIG. 2 shows western blot images indicating the intracellular and extracellular ZHD101 expression by the transformed *P. pastoris* cultured for the indicated time in a molasses-containing medium with or without methanol added.

FIG. 2 shows western blot images indicating the intracellular and extracellular ZHD101 expression by the transformed P. pastoris cultured in the molasses-containing medium with or without methanol. According to FIG. 2, the yeast cultured in the molasses-containing medium with no methanol added produced both intracellular and extracellular ZHD101 in a detectable amount after incubation for less than 72 hours. The addition of methanol to the molasses-containing medium led to high production of the intracellular and extracellular ZHD101 after incubation for 24 hours and 72 hours, respectively. This result indicates that the molasses-containing medium compared to the BMMY medium is sufficient for the efficient production of ZHD101 by the transformed P. pastoris, and the addition of methanol may further decrease the incubation time required for ZHD101 production.

Figure 3A:
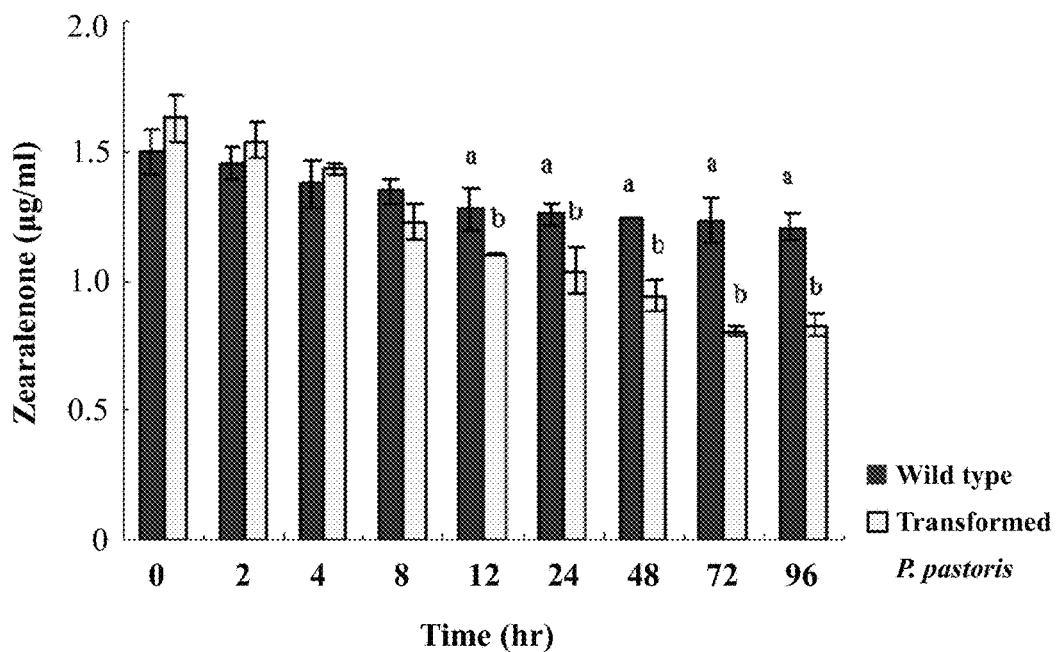
FIG. 3A shows that the expressed recombinant ZHD101 in the culture of wild type or transformed *P. pastoris* exhibited hydrolytic activity against zearalenone; "a" and "b" represent a significant difference in zearalenone levels between the wild type and the transformed *P. pastoris* cultures collected at the indicated time.
Figure 3B:
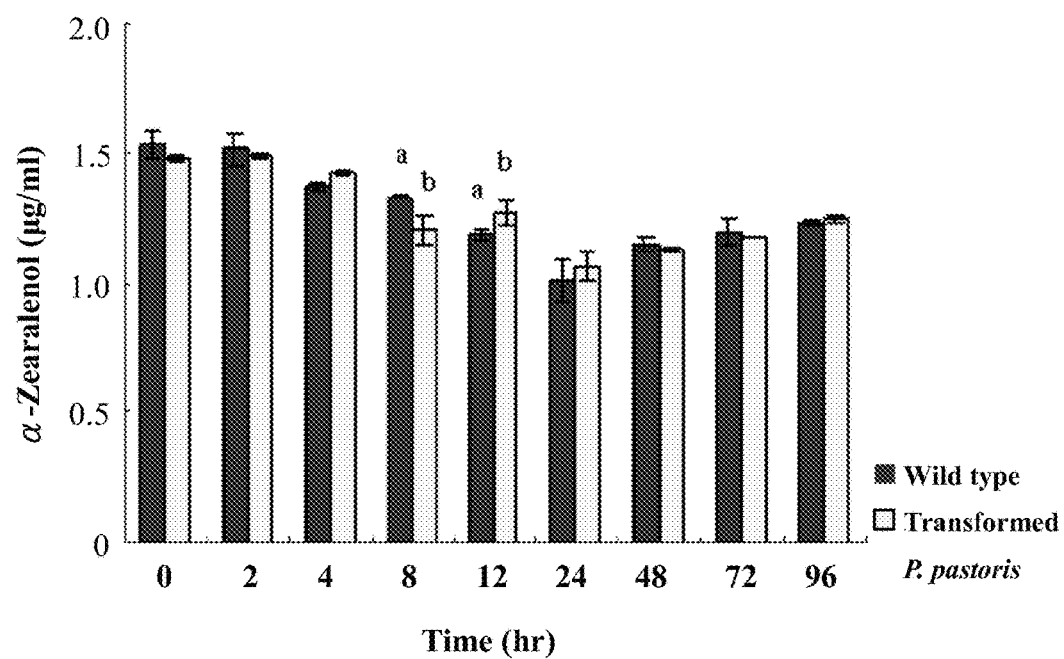
FIG. 3B shows that the expressed recombinant ZHD101 in the culture of wild type or transformed *P. pastoris* exhibited hydrolytic activity against α-zearalenol; "a" and "b" represent a significant difference in α-zearalenol levels between the wild type and the transformed *P. pastoris* cultures collected at the indicated time.

The enzymatic activity of the BMMY-based and methanol-added culture of transformed P. pastoris expressing the recombinant ZHD101 protein was assessed by monitoring the degradation of zearalenone and α-zearalenol which were added to the culture. A culture of untransformed P. pastoris (denoted as wild type) prepared similarly was used as control. As shown in FIG. 3A, zearalenone levels significantly decreased in both the transformed and wild-type P. pastoris cultures after 12 hours of the hydrolytic reaction, and a more significant decrease was observed in the transformed P. pastoris culture, indicating that the expressed recombinant ZHD101 protein exhibited hydrolytic activity against zearalenone. As shown in FIG. 3B, α-zearalenol levels also decreased in the two cultures within 12 hours of the hydrolytic reaction, suggesting that the recombinant ZHD101 protein also had hydrolytic activity against α-zearalenol.

Example 2

Industrial-Scale Production of Zearalenone Hydrolase

The P. pastoris yeast strain GS115, transformed with the ZHD101 expression vector, was inoculated into about 3 to 5 mL of fresh YPD medium and incubated at 28° C. to 30° C. with agitation at 150 rpm for 24 hours, and 300 μl of this yeast culture was then seeded into 250 ml of the BMGY medium to obtain a first culture which was then incubated at 28° C. to 30° C. with agitation at 100 to 150 rpm overnight. Large numbers of the first culture were prepared for scaling up the ZHD101 production. After reaching an OD600 value of about 2, the first culture preparations were centrifuged at 5000×g for 5 minutes at 4° C., and the resultant cell pellet was collected and resuspended in the molasses-containing medium (TABLE 1) to obtain a second culture. After diluted to an OD600 value of about 1, the second culture (about 6 L), supplemented with 0.25 to 0.75% (v/v), preferably 0.5% (v/v) methanol and an antifoaming agent, was incubated at 28° C. to 30° C. in a 10 L fermentation chamber for 72 hours with the dissolved oxygen maintained at 20% and the agitation at 150 rpm. During the fermentation process, the yeast culture was collected every 24 hours for measuring the OD value and generating a yeast growth curve. The ZHD101 protein with the zearalenone-degrading ability was found to be efficiently produced by the transformed P. pastoris incubated in the molasses-containing medium during the industrial fermentation process.

Conventional biochemical techniques, such as nickel chelate affinity chromatography and protein fractionation based on molecular weight, may be employed to purify the intracellular or extracellular ZHD101 protein from the yeast cells or the yeast culture medium.

In conclusion, the method of the present invention utilizes the molasses-containing medium to induce the high production of zearalenone hydrolase by yeast in three days. Therefore, the present invention provides a new strategy to prepare zearalenone hydrolase efficiently at low expenses.

```
SEQUENCE LISTING

<110> Life Rainbow Biotech Co., Ltd.
<120> METHOD OF PREPARING ZEARALENONE HYDROLASE
<130> 106F0486-IE
<160> 1
<170> PatentIn version 3.5
<210> 1
<211> 795
<212> DNA
<213> Clonostachys rosea
<400> 1
atgcgcactc gcagcacaat ctcgaccccg aatggcatca cctggtacta tgagcaggag    60
ggtactggac ccgacgttgt cctcgtcccc gatggcctcg gagaatgcca gatgtttgac   120
agctccgtgt cgcaaattgc tgcccaaggc tttcgggtca ccacgtttga catgcccgga   180
atgtcccggt ctgcgaaggc accacccgag acctacactg aggtcacggc cagaagctg    240 gcttcctatg tcatctccat cctggatgct cttgacatca agcacgctac tgtctggggc   300
tgcagctcag gagcttccac cgtcgtggcg ctgttgctcg gttaccccga caggatacgc   360
aacgccatgt gccacgaact gccaacaaag ctactggacc cctttcaaa caccgctgtg    420 ctcgaagacg aggaaatctc aaagatcctg gccaatgtaa tgttgaacga cgtgtctgga   480
ggctcggagg cgtggcaagc catggggac gaggtgcacg cgagactgca caagaactac    540
ccggtttggg ctcgaggata ccctcgcact attcctccct cagctccggt taaggatctg   600
gaggctctgc gtgggaagcc cctggactgg actgtcggcg ctgcgacacc aaccgagtct   660
ttctttgaca acattgttac cgctaccaag gctggtgtca acattgggtt gcttccaggg   720
atgcatttcc cttatgtttc ccacccggac gttttcgcta aatatgttgt ggaaactacg   780
cagaagcatc tttga                                                    795
```

---

```
SEQUENCE LISTING

<160> NUMBER OF SEQ ID NOS: 1

<210> SEQ ID NO 1
<211> LENGTH: 795
<212> TYPE: DNA
<213> ORGANISM: Clonostachys rosea

<400> SEQUENCE: 1
atgcgcactc gcagcacaat ctcgaccccg aatggcatca cctggtacta tgagcaggag     60
ggtactggac ccgacgttgt cctcgtcccc gatggcctcg gagaatgcca gatgtttgac    120
agctccgtgt cgcaaattgc tgcccaaggc tttcgggtca ccacgtttga catgcccgga    180
atgtcccggt ctgcgaaggc accacccgag acctacactg aggtcacggc cagaagctg     240 gcttcctatg tcatctccat cctggatgct cttgacatca agcacgctac tgtctggggc    300
tgcagctcag gagcttccac cgtcgtggcg ctgttgctcg gttaccccga caggatacgc    360
aacgccatgt gccacgaact gccaacaaag ctactggacc cctttcaaa caccgctgtg     420 ctcgaagacg aggaaatctc aaagatcctg gccaatgtaa tgttgaacga cgtgtctgga    480
ggctcggagg cgtggcaagc catggggac gaggtgcacg cgagactgca caagaactac     540
ccggtttggg ctcgaggata ccctcgcact attcctccct cagctccggt taaggatctg    600
gaggctctgc gtgggaagcc cctggactgg actgtcggcg ctgcgacacc aaccgagtct    660
ttctttgaca acattgttac cgctaccaag gctggtgtca acattgggtt gcttccaggg    720
```

-continued

```
atgcatttcc cttatgtttc ccacccggac gttttcgcta aatatgttgt ggaaactacg        780
cagaagcatc tttga                                                        795
```

What is claimed is:

1. A method of preparing zearalenone hydrolase, comprising culturing a *Pichia pastoris* cell carrying an expression vector comprising a methanol inducible promoter and the nucleotide sequence of SEQ ID NO:1 in a medium to express a protein of the zearalenone hydrolase, wherein the medium comprises 20 to 25% molasses by weight and methanol.

2. The method of claim 1, wherein the methanol in the medium is at a concentration of 0.25 to 0.75%.

3. The method of claim 1, wherein the *Pichia pastoris* cell is cultured at 28° C. to 30° C. for 24 to 72 hours.

4. The method of claim 1, wherein the *Pichia pastoris* cell is cultured with agitation at 100 to 150 rpm.

5. The method of claim 1, wherein the medium further comprises urea, ammonium dihydrogen phosphate, thiamine, or any combinations thereof.

6. The method of claim 1, further comprising isolating the zearalenone hydrolase from the *Pichia pastoris* cell or the medium after the culturing.

7. The method of claim 6, wherein the zearalenone hydrolase is isolated by lysing the *Pichia pastoris* cell and collecting a supernatant of a cell lysate obtained therefrom.

* * * * *